United States Patent [19]

Tamao et al.

[11] Patent Number: 5,141,947
[45] Date of Patent: Aug. 25, 1992

[54] FIBRINOLYSIS-ENHANCING AGENTS

[75] Inventors: Yoshikuni Tamao; Ryoji Kikumoto, both of Machida, Japan

[73] Assignee: Mitsubishi Kasei Corporation, Tokyo, Japan

[21] Appl. No.: 758,208

[22] Filed: Sep. 12, 1991

Related U.S. Application Data

[63] Continuation of Ser. No. 259,591, Oct. 19, 1988, abandoned, which is a continuation of Ser. No. 790,196, Oct. 22, 1985, abandoned.

[30] Foreign Application Priority Data

Nov. 6, 1984 [JP] Japan .................. 59-233567

[51] Int. Cl.$^5$ ............... C07D 215/14; C07D 213/24; C07D 403/12
[52] U.S. Cl. ................... 514/314; 514/311; 514/319
[58] Field of Search ............ 514/311, 314, 319

[56] References Cited

U.S. PATENT DOCUMENTS

| | | | |
|---|---|---|---|
| 3,875,005 | 4/1975 | Belloc et al. | 424/94 |
| 3,919,414 | 11/1975 | Herrin et al. | 424/94 |
| 4,073,916 | 2/1978 | Okamoto et al. | 514/822 |
| 4,258,192 | 3/1981 | Okamoto et al. | 546/166 |
| 4,532,129 | 7/1985 | Comi et al. | 424/94 |

*Primary Examiner*—David B. Springer
*Attorney, Agent, or Firm*—Oblon, Spivak, McClelland, Maier & Neustadt

[57] ABSTRACT

Disclosed herein is a fibrinolysis-enhancing agent comprising, as an effective ingredient, an $N^2$-arylsulfonyl-L-arginine amide represented by the general formula (I):

$$\begin{array}{c} NH \\ \diagdown \\ C-NH-(CH_2)_3-CHCOR^1 \\ \diagup \qquad\qquad\qquad | \\ NH_2 \qquad\qquad\qquad NHSO_2R^2 \end{array} \quad (I)$$

wherein $R^1$ is a group of the formula:

$$-N\begin{pmatrix} R^3 \\ CH_2COOH \end{pmatrix} \quad \text{or} \quad -N\begin{pmatrix} COOH \\ R^4 \end{pmatrix}$$

where $R^3$ is an alkyl group having 3 to 5 carbon atoms or an alkoxyalkyl group having 2 to 4 carbon atoms and $R^4$ is an alkyl group having 1 to 3 carbon atoms; and $R^2$ is a group of the formula:

[structures with $R^5$, $R^6$ and $R^7$]

where $R^5$ and $R^6$ are independently hydrogen atom, methyl group or methoxy group provided that they cannot be hydrogen atoms simultaneously, and $R^7$ is an alkyl group having 1 to 3 carbon atoms; or a salt thereof. The agent is used in combination with a plasminogen activator.

13 Claims, 1 Drawing Sheet

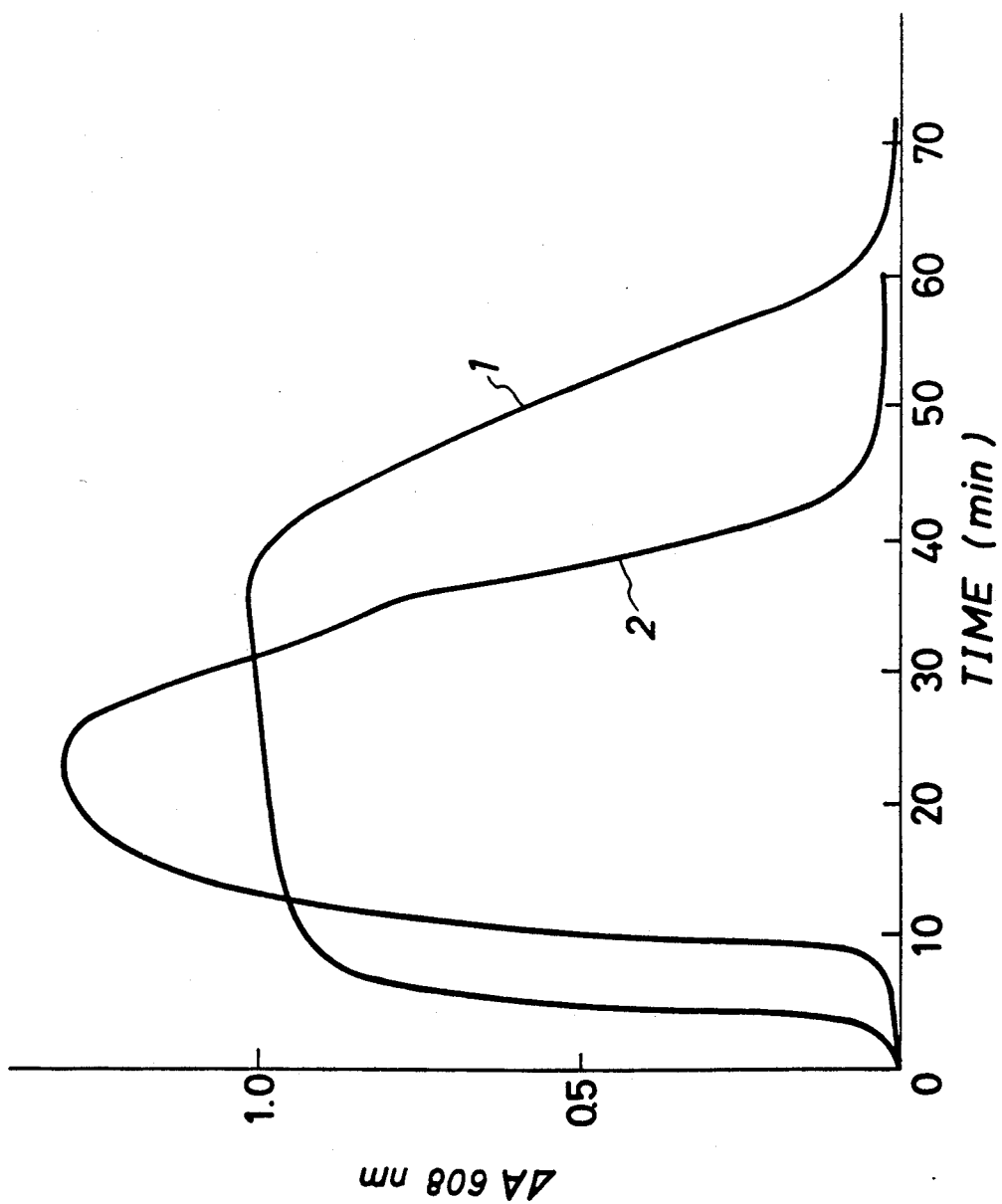

FIBRINOLYSIS-ENHANCING AGENTS

This application is a continuation of application Ser. No. 06/259,591, filed Oct. 19, 1988, which is a continuation of Ser. No. 06/790,196, filed Oct. 22, 1985, both now abandoned.

FIELD OF THE INVENTION

This invention relates to fibrinolysis-enhancing agents.

DESCRIPTION OF THE PRIOR ART

Thrombus is generated by fibrin formation and platelet aggregation in blood vessels. It may cause cerebral infarction, peripheral arteriovenous thrombosis, myocardial infarction and the like.

Thrombus is primarily composed of a protein, called fibrin, which is decomposed by plasmin, a proteolytic enzyme derived from plasminogen by the action of an activator. This process is called fibrinolysis. Such an activator is known as a thrombolytic agent which dissolves thrombi by the fibrinolytic and includes tissue plasminogen activator (p-TA), urokinase (UK), streptokinase (SK) and others.

SUMMARY OF THE INVENTION

In order to reduce an amount of such a thrombolytic agent used in the fibrinolysis and further improve the clinical effect by decreasing the time of period for dissolving thrombi, i.e. by an immediate effect, various attempts have been made by the present inventors. Now, we have found that such a purpose can be attained by a novel combination of the activator with a specific arginine derivative which inhibits the blood coagulation system.

There is provided in accordance with the invention a fibrinolysis-enhancing agent comprising, as an effective ingredient, an $N^2$-arylsulfonyl-L-arginine amide represented by the general formula (I):

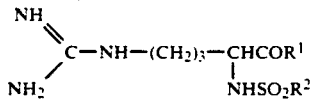

wherein $R^1$ is a group of the following formula:

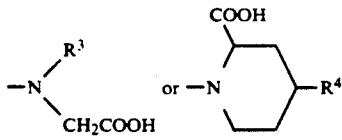

where $R^3$ is an alkyl group having 3 to 5 carbon atoms or an alkoxyalkyl group having 2 to 4 carbon atoms in total and $R^4$ is an alkyl group having 1 to 3 carbon atoms; and $R^2$ is a group of the following formula:

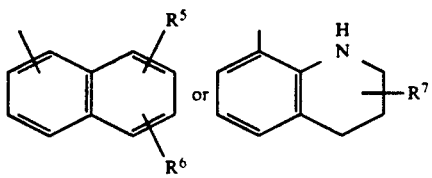

where $R^5$ and $R^6$ are independently hydrogen atom, methyl group or methoxy group but cannot be hydrogen atom simultaneously, and $R^7$ is an alkyl agoup having 1 to 3 carbon atoms; or a salt thereof.

DESCRIPTION OF THE INVENTION

The invention will be described in detail hereinbelow.

The $N^2$-arylsulfonyl-L-arginine amides used in the invention are represented by the following general formula (I):

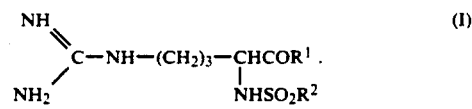

In the general formula (I), $R^1$ represents a group of the following formula:

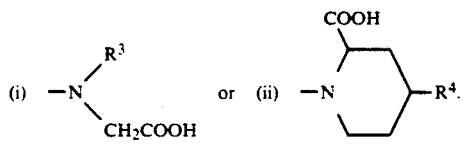

The group $R^3$ is an alkyl group having 3 to 5 carbon atoms or an alkoxyalkyl group having 2 to 4 carbon atoms in total. Butyl is a particularly preferred alkyl group. The alkoxyalkyl group includes methoxyethyl, ethoxyethyl and ethoxymethyl groups with methoxyethyl group being prticularly preferred. The group $R^4$ is an alkyl group having 1 to 3 carbon atoms. Methyl or ethyl group is particularly preferred.

In the general formula (I), $R^2$ represents a group of the following formula:

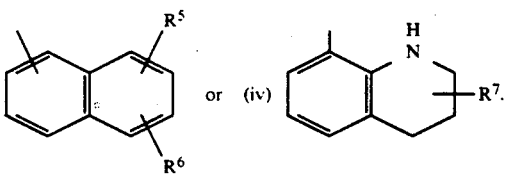

The position of the bonding between the naphthyl group in the formula (iii) and the sulfonyl group in the formula (I) is not limited. The groups $R^5$ and $R^6$ are independently hydrogen atom, methyl group or an alkoxy group such as methoxy; however, they cannot be hydrogen atom simultaneously. The group $R^7$ is an alkyl group having 1 to 3 carbon atoms; methyl and ethyl groups are particularly preferred.

When $R^1$ is the group (ii) in the general formula (I), the optically active (2R, 4R)-4-alkyl-2-carboxypiperidino group is most preferred.

Examples of the compounds which may be preferably used in the invention include:

1-[$N^2$-(3-methyl-1,2,3,4-tetrahydro-8-quinolinesulfonyl)-L-arginyl]-4-methyl-2-piperidinecarboxylic acid;

1-[$N^2$-(3-methyl-1,2,3,4-tetrahydro-8-quinolinesulfonyl)-L-arginyl]-4-ethyl-2-piperidinecarboxylic acid;

1-[$N^2$-(3-ethyl-1,2,3,4-tetrahydro-8-quinolinesulfonyl)-L-arginyl]-4-methyl-2-piperidinecarboxylic acid;

1-[N²-(3-ethyl-1,2,3,4-tetrahydro-8-quinolinesulfonyl)-
  L-arginyl]-4-ethyl-2-piperidinecarboxylic acid;
1-[N²-(6,7-dimethoxy-2-naphthylsulfonyl)-L-arginyl]-4-
  methyl-2-piperidinecarboxylic acid;
1-[N²-(6,7-dimethyl-2-naphthylsulfonyl)-L-arginyl]-4-
  methyl-2-piperidinecarboxylic acid;
1-[N²-(7-methoxynaphthalene-2-sulfonyl-L-arginyl]-4-
  methyl-2-piperidinecarboxylic acid;
1-[N²-(7-methylnaphthalene-2-sulfonyl-L-arginyl]-4-
  methyl-2-piperidinecarboxylic acid;
1-[N²-(6,7-dimethoxynaphthalene-2-sulfonyl-L-
  arginyl]-4-ethyl-2-piperidinecarboxylic acid;
1-[N²-(7-methylnaphthalene-2-sulfonyl-L-arginyl]-4-
  isopropyl-2-piperidinecarboxylic acid; and
1-[N²-(4,6-dimethoxynaphthalene-2-sulfonyl-L-
  arginyl]-4-methyl-2-piperidinecarboxylic acid.

Corresponding optical isomers of the above-listed compounds, e.g. (2R, 4R)-4-alkyl-2-piperidinecarboxylic acid derivatives, may also be employed in the invention.

Examples of glycine type compounds within the scope of the general formula (I) where $R^1$ is the group (i) include:
[N²-(6,7-dimethoxynaphthalene-2-sulfonyl)-L-arginyl]-
  N-(2-methoxyethyl)glycine;
[N²-(6,7-dimethylnaphthalene-2-sulfonyl)-L-arginyl]-
  N-(2-methoxyethyl)glycine; and
[N²-(7-methoxynaphthalene-2-sulfonyl)-L-arginyl]-N-
  butylglycine.

Salts of the above listed compounds can also be employed for a fibrinolysis-enhancing agent of the present invention. Acids which may be used to form such salts include hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic and other acids. Bases which can be utilized in the invention may be sodium hydroxide, potassium hydroxide, ammonium hydroxide, triethylamine, procaine, dibenzylamine, 1-ephenamine, N,N'-dibenzylethylene-diamine, N-ethylpiperidine or the like.

The compounds represented by the general formula (I) are known and their preparation is described in detail in Japanese Patent Application Laying Open (KOKAI) No. 97934/77 and European Patent Application Publication No. 8746 published Mar. 19, 1980.

It has been shown that the compounds represented by the general formula (I) may suppress the activity of thrombin and thereby inhibit the formation of fibrin and the aggregation of platelets, and that they can inhibit the formation of thrombus in various animal models.

For instance, clinical effects on various thrombosis of (2R, 4R)-1-[N²-(3-methyl-1,2,3,4-tetrahydro-8-quinolinesulfonyl)-L-arginyl]-4-methyl-2-piperidinecarboxylic acid having the following formula (Ia) are now being investigated:

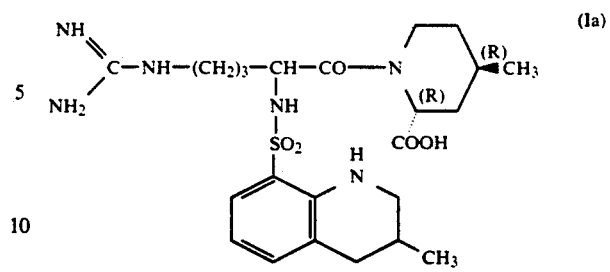

The fibrinolysis-enhancing agents according to the invention are employed in the fibrinolysis using a plasminogen activator as listed below. The fibrinolysis-enhancing agent and the plasminogen activator may be administered at the same time or, alternatively, successively in any order with an appropriate interval, usually up to several hours.

The plasminogen activator used together with the fibrinolysis-enhancing agent of the present invention is a substance which activates plasminogen and converts it into plasmin. Illustrative examples are single or double chain tissue plasminogen activator (t-PA), high or low molecular weight urokinase (UK), prourokinase, streptokinase (SK) and others.

According to the present invention, the fibrinolysis-enhancing agent can be used in a wide range of amount depending on the type of the plasminogen activator used and other factors: for example, if t-PA is used in combination with the arginine derivative of the general formula (I) for continuous intravenous injections, the weight ratio of t-PA to the arginine derivative will generally be in the range of 1:0.1 to 1:100.

The enhancing agent according to the invention may be used alone or in combination with a pharmaceutically acceptable carrier, the amount of which can be determined in accordance with administration routes, schemes and others.

The dose amount may depend on the age, body weight, state of symptom and the like of a patient to be treated. The enhancing agent is preferably administered parenterally.

The dose amount of the active ingredient in the fibrinolysis-enhancing agent of the invention, N²-arylsulfonyl-L-arginine amide or salt thereof, will generally be in the range of 0.01 to 100 mg/kg per day, preferably 0.1 to 10 mg/kg per day, for parenteral administration, and 1 to 200 mg/kg per day, preferably 5 to 20 mg/kg per day, for oral administration.

For parenteral administration, the agent is used in any sterilized liquid form, such as a solution and suspension. For rectal or oral administration, it can be employed in the form of tablets, capsules, powder, granules, liquid, elixir or the like. Such a dosage unit form may comprise a pharmaceutically acceptable, non-toxic, solid or liquid carrier.

When administered parenterally, e.g., injected intramuscularly, intravenously or subcutaneously, there is utilized a sterile solution to which a solute, such as sodium chloride, glucose and the like, is added so as to make it isotonic.

Solvents suitable for injection include sterile water, physiological saline, glucose, liquids and electrolyte solutions for intravenous injection, and others. These injectable solutions generally comprise 0.005 to 10% by weight, preferably 0.01 to 5% by weight, of an effective ingredient.

The fibrinolysis-enhancing agent according to the present invention will significantly enhance the fibrinolysis of plasma clots by a plasminogen activator and this enhancement may be achieved even at a low concentration while its effects are dependent on the concentration. Thus, the agent can dissolve the plasma clots in a short time and the amount of the activator used can be reduced.

EXAMPLES

The following examples will be given by way of illustration of the fibrinolysis-enhancing agents of the invention but are not intended to limit the scope of the invention.

The arginine derivative of the formula (Ia) above was prepared in accordance with Example 2 described in the European Patent Application Publication No. 8746. The acute toxicity, $LD_{50}$, of the arginine derivative was 211 mg/kg when administered intravenously to male mice weighing 20 g.

The arginine derivative, hereinafter referred to as "the compound (Ia)", was used in the following Examples 1 and 2.

Example 1

One part by volume of 3.8% sodium citrate solution was added to 9 parts by volume of the venous blood of a healthy person and centrifuged at 3,000 rpm for 15 minutes to collect the plasma.

There was placed 0.6 ml of the plasma into a spectrophotometric microcell having a path length of 10 mm and a path width of 2 mm. After adding 0.015 ml of physiological saline containing the compound (Ia) in various concentrations, the cell was held in the cell holder of a spectrophotometer, Hitachi 220 A, which was maintained at 37° C. and incubated for 5 minutes. Into the cell, there was added 0.025 ml of a solution of 8.0 µg/ml t-PA (tissue plasminogen activator) or 3,000 international units per ml high molecular weight UK, urokinase manufactured by The Green Cross Corporation, and 0.06 ml of 0.25M $CaCl_2$ solution. Changes in the absorbance at 608 nm were recorded at 37° C. every one minute. Thus, the coagulation and fibrinolysis of the plasma were measured with the time lapse.

The results of a typical experiment are shown in the sole FIGURE. In the FIGURE, the ordinate represents the difference of absorbance ($\Delta A$) at 608 nm and the abscissa represents the time in minutes. As seen from the FIGURE the absorbance increased with the progress of coagulation and decreased with the dissolution of fibrin.

The effects of the compound (Ia) on the dissolution time and the coagulation time were measured on the plasma from five healthy persons. The results for the fibrinolysis by UK are shown in Table 1, and those by t-PA in Table 2. Values in Tables are expressed in the average+S.E.M.

The coagulation time is defined as a time period from the time 0 at which $CaCl_2$ solution is added to a coagulation initiation time at which the absorbance has increased to a value larger by 0.025 than the value at the time 0: i.e., delta A is 0.025. The dissolution time is defined as a time period from the coagulation initiation time to a fibrinolysis termination time at which the absorbance has decreased to a value 10% that of the maximum value.

As shown in Tables, by adding 0.1 µM or 0.3 µM of the compound (Ia) the dissolution time was significantly reduced in both the fibrinolysis by UK and t-PA in comparison with no addition of the compound. The coagulation time was extended to 1.5 to 3 times as long as that observed without addition of the compound.

TABLE 1

Enhancing Activity of Compound (Ia) on Fibrinolysis of Plasma Aggregation Effected by UK; 0.6 ml of Plasma in the Total Volume (0.7 ml)

| Compound | Concentration (µM) | Number of Experiments | Dissolution Time (min) | Coagulation Time (min) |
|---|---|---|---|---|
| None (control) | — | 5 | 44.3 ± 5.2 | 5.5 ± 0.8 |
| Compound (Ia) | 0.1 | 5 | 28.2 ± 5.2 | 8.8 ± 1.1* |
|  | 0.3 | 5 | 24.6 ± 4.3* | 10.2 ± 1.4* |

*$P < 0.05$ (t-test carried out to compare with the control)

TABLE 2

Enhancing Activity of Compound (Ia) on Fibrinolysis of Plasma Aggregation Effected by t-PA; 0.6 ml of Plasma in the Total Volume (0.7 ml)

| Compound | Concentration (µM) | Number of Experiments | Dissolution Time (min) | Coagulation Time (min) |
|---|---|---|---|---|
| None (control) | — | 5 | 44.1 ± 2.4 | 5.7 ± 0.8 |
| Compound (Ia) | 0.1 | 5 | 33.0 ± 2.0** | 10.6 ± 2.0 |
|  | 0.3 | 5 | 32.0 ± 2.8* | 13.8 ± 2.8* |

**$P < 0.01$;
*$P < 0.05$ (t-test carried out to compare with the control)

Example 2

The procedures of Example 1 were repeated except that a less amount of plasma was used. Thus, in the same manner as Example 1, there was collected 0.15 ml of plasma to which 0.1 ml of physiological saline containing the compound (Ia) in various concentrations was added, the total volume was adjusted to 0.375 ml, the resulting mixture was incubated at 37° C. for 5 minutes, 0.025 ml of a solution of 1.6 µg/ml t-PA or 500 international units per ml high molecular weight UK and 0.3 ml of 0.025M $CaCl_2$ solution were added, and the coagulation and fibrinolysis of the plasma were measured with the time lapse to determine the coagulation time and dissolution time. The results on five healthy persons are shown in Table 3 for the fibrinolysis by UK and in Table 4 for t-PA.

The fibrinolysis was enhanced by the addition of the compound (Ia) even in an amount as low as 0.01 µM, and the fibrinolysis enhancing activity increased depending on the concentration. At 0.3 µM of the compound (Ia), the dissolution time decreased to about ¼ of the time without addition in the fibrinolysis by UK and to about ⅓ in t-PA.

The coagulation time was prolonged slightly at the minimum concentration used (0.01 µM) of the compound (Ia) and to 2 to 3 times at the maximum concentration used (0.3 µM) in both cases of UK and t-PA.

TABLE 3

Enhancing Activity of Compound (Ia) on Fibrinolysis of Plasma Aggregation Effected by UK; 0.15 ml of Plasma in the Total Volume (0.7 ml)

| Compound | Concentration (µM) | Number of Experiments | Dissolution Time (min) | Coagulation Time (min) |
|---|---|---|---|---|
| None | — | 5 | 80.3 ± 14.7 | 4.0 ± 0.4 |

TABLE 3-continued

Enhancing Activity of Compound (Ia) on Fibrinolysis of Plasma Aggregation Effected by UK; 0.15 ml of Plasma in the Total Volume (0.7 ml)

| Compound | Concentration ($\mu$M) | Number of Experiments | Dissolution Time (min) | Coagulation Time (min) |
|---|---|---|---|---|
| (control) | | | | |
| Compound (Ia) | 0.01 | 5 | 63.8 ± 11.8 | 4.9 ± 0.6 |
| | 0.03 | 5 | 35.9 ± 5.7* | 5.5 ± 0.4* |
| | 0.1 | 5 | 23.4 ± 2.2** | 7.4 ± 0.8** |
| | 0.3 | 5 | 22.5 ± 1.3** | 9.9 ± 0.8*** |

***$P < 0.001$.
**$P < 0.01$;
*$P < 0.05$ (t-test carried out to compare with the control)

TABLE 4

Enhancing Activity of Compound (Ia) on Fibrinolysis of Plasma Aggregation Effected by t-PA; 0.15 ml of Plasma in the Total Volume (0.7 ml)

| ComPound | Concentration ($\mu$M) | Number of Experiments | Dissolution Time (min) | Coagulation Time (min) |
|---|---|---|---|---|
| None (control) | — | 5 | 78.4 ± 10.8 | 3.8 ± 0.2 |
| Compound (Ia) | 0.01 | 5 | 64.1 ± 10.2 | 4.5 ± 0.2* |
| | 0.03 | 5 | 51.6 ± 7.7 | 5.0 ± 0.2** |
| | 0.1 | 5 | 34.5 ± 5.2** | 6.7 ± 0.3*** |
| | 0.3 | 5 | 26.6 ± 2.4** | 9.0 ± 0.3*** |

***$P < 0.001$.
**$P < 0.01$.
*$P < 0.05$ (t-test carried out to compare with the control)

Example 3

Activities of arginine derivatives having the thrombin-inhibiting effect and the structural formula shown below on the fibrinolysis by t-PA were estimated in the same manner as Example 2. The results are shown in Table 5. As seen from Table 5, the dissolution time was reduced to ½ to ⅓ at 0.3 $\mu$M of each derivative.

Structural formulae of arginine derivatives:

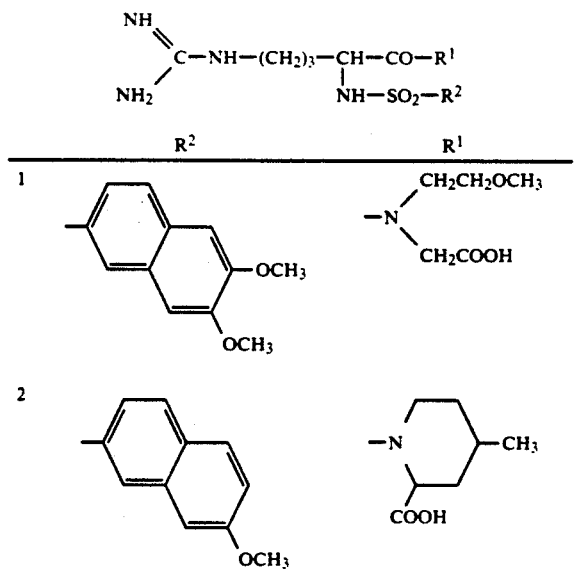

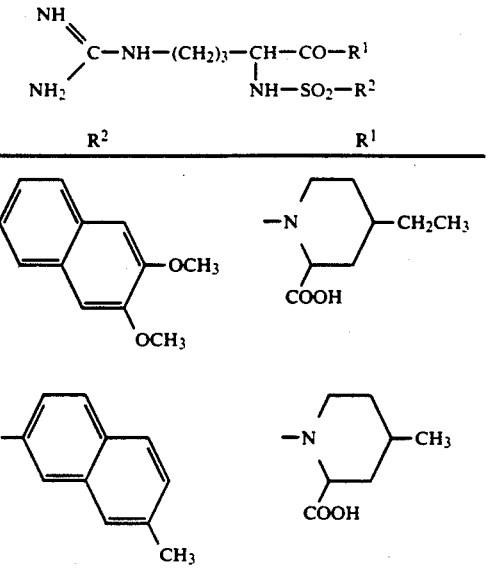

TABLE 5

Enhancing Activity of Arginine Derivatives on Fibrinolysis of Plasma Aggregation Effected by t-PA; 0.15 ml of Plasma in the Total Volume (0.7 ml)

| Compound Number | Concentration ($\mu$M) | Dissolution Time (min) | Coagulation Time (min) |
|---|---|---|---|
| None (control) | — | 95.7 | 2.9 |
| 1 | 0.3 | 55.4 | 3.2 |
| 2 | 0.3 | 36.5 | 4.1 |
| 3 | 0.3 | 53.4 | 3.2 |
| 4 | 0.3 | 50.5 | 3.1 |

Example 4

The carotid artery of a rabbit was exposed from the surrounding tissue under anesthesia by pentobarbital. The exposed artery was surrounded with absorbent cotton soaked with glacial acetic acid and allowed to stay for 3 hours to form thrombus by the damage done to the endorthelium. The thus formed thrombus was tested for dissolution.

Immediately after removing out the cotton, physiological saline in which the substance to be tested had been dissolved was injected through the femoral vein. The infusion was continued over 2 hours. After the infusion, the arterial segment wherein the thrombus had been formed was cut out and the thrombus mass was removed out under a microscope. The thrombus was dissolved in alkali and the protein was quantitatively measured by phenol method.

The results in Table 6 show that the administration of t-PA (0.48 mg/kg) or the compound (Ia) (1.2 mg/kg) alone gave no thrombolytic effect; while on the contrary the administration of both t-PA (0.48 mg/kg) and the compound (Ia) (1.2 mg/kg) caused the dissolution of about 90% thrombus. The thrombolytic effect was higher than that of the administration of 0.96 mg/kg t-PA alone.

TABLE 6

Enhancing Activity of Compound (Ia) in in vivo Thrombolysis by t-PA

| Administered Material | Number of Experiments | Thrombus Protein (mg) |
|---|---|---|
| Physiological Saline (control) | 5 | 1.97 ± 0.38 |
| t-PA, 0.48 mg/kg | 4 | 2.45 ± 0.81 |
| t-PA, 0.96 mg/kg | 4 | 0.40 ± 0.16 |
| Compound (Ia), 1.2 mg/kg | 4 | 2.03 ± 0.55 |
| t-PA, 0.48 mg/kg + Compound (Ia), 1.2 mg/kg | 4 | 0.19 ± 0.05 |

What is claimed is:

1. A fibrinolysis-enhancing composition, comprising: a plasminogen activator in combination with a fibrinolysis enhancing agent which is an $N^2$-arylsulfonyl-L-arginine amide of formula (I):

$$\underset{NH_2}{\overset{NH}{\diagdown}}C-NH-(CH_2)_3-\underset{NHSO_2R^2}{\overset{|}{C}}HCOR^1$$

wherein $R^1$ is a group of the formula:

$$-N\underset{CH_2COOH}{\overset{R^3}{\diagdown}} \quad \text{or} \quad -N\underset{\phantom{xx}}{\diagdown}R^4 \text{ (with COOH)}$$

(i)          (ii)

wherein $R^3$ is an alkyl group having 3 to 5 carbon atoms or an alkoxyalkyl group having 2 to 4 carbon atoms in total and $R^4$ is an alkyl group having 1 to 3 carbon atoms; and $R^2$ is a group of the formula:

(naphthalene with $R^5$, $R^6$)    or    (tetrahydroquinoline with $R^7$)

(iii)          (iv)

wherein $R^5$ and $R^6$ are independently hydrogen, methyl or methoxy, provided that they cannot simultaneously be hydrogen atoms and provided that when $R^2$ is radical (iii) $R^1$ is radical (ii), and $R^7$ is an alkyl group having 1 to 3 carbon atoms; or a pharmaceutically acceptable salt thereof.

2. The composition of claim 1, wherein group $R^3$ is butyl or methoxyethyl.

3. The composition of claim 1, wherein group $R^4$ is methyl or ethyl.

4. The composition of claim 1, wherein group $R^7$ is methyl or ethyl.

5. The composition of claim 1, wherein group $R^1$ is (2R,4R)-4-alkyl-2-carboxypiperidino.

6. The composition of claim 1, wherein said fibrinolysis enhancing agent is 1-[$N^2$-(3-methyl-1,2,3,4-tetrahydro-8-quinolinesulfonyl)-L-arginyl]-4-methyl-2-piperidinecarboxylic acid.

7. The composition of claim 1, wherein said fibrinolysis enhancing agent is 1-[$N^2$-(7-methoxynaphthalene-2-sulfonyl-L-arginyl]-4-methyl-2-piperidinecarboxylic acid.

8. The composition of claim 1, wherein said fibrinolysis enhancing agent is 1-[$N^2$-6,7-dimethoxynaphthalene-2-sulfonyl-L-arginyl]-4-ethyl-2-piperidinecarboxylic acid.

9. The composition f claim 1, wherein said fibrinolysis enhancing agent is 1-[$N^2$-(7-methylnaphthalene-2-sulfonyl-L-arginyl]-4-methyl-2-piperidinecarboxylic acid.

10. The composition of claim 1, wherein the active ingredients of said composition are used in combination with a pharmaceutically acceptable carrier.

11. The composition of claim 1, wherein, when said plasminogen activator is tissue plasminogen activator, the weight ratio of tissue plasminogen activator to said arginine derivative ranges from 1:0.1 to 1:100.

12. The composition of claim 1, wherein said plasminogen activator is tissue plasminogen activator, urokinase, prourokinase or streptokinase.

13. A method of treating thrombosis, which comprises:

administering to a patient in need of thrombosis treatment a fibrinolytically effective amount of a composition comprising a plasminogen activator in combination with a fibrinolysis enhancing agent which is an $N^2$-arylsulfonyl-L-arginine amine of formula (I):

$$\underset{NH_2}{\overset{NH}{\diagdown}}C-NH-(CH_2)_3-\underset{NHSO_2R^2}{\overset{|}{C}}HCOR^1$$

wherein $R^1$ is a group of the formula:

$$-N\underset{CH_2COOH}{\overset{R^3}{\diagdown}} \quad \text{or} \quad -N\underset{\phantom{xx}}{\diagdown}R^4 \text{ (with COOH)}$$

(i)          (ii)

wherein $R^3$ is an alkyl group having 3 to 5 carbon atoms or an alkoxyalkyl group having 2 to 4 carbon atoms in total and $R^4$ is an alkyl group having 1 to 3 carbon atoms; and $R^2$ is a group of the formula:

(naphthalene with $R^5$, $R^6$)    or    (tetrahydroquinoline with $R^7$)

(iii)          (iv)

wherein $R^5$ and $R^6$ are independently hydrogen, methyl or methoxy, provided that they cannot simultaneously be hydrogen atoms and provided that when $R^2$ is radical (iii) $R^1$ is radical (ii), and $R^7$ is an alkyl group having 1 to 3 carbon atoms; or a pharmaceutically acceptable salt thereof.

* * * * *